(12) United States Patent
Kumar (10) Patent No.: US 10,449,226 B2
(45) Date of Patent: Oct. 22, 2019

(54) COMBINATION

(71) Applicant: Novartis AG, Basel (CH)

(72) Inventor: Rakesh Kumar, Collegeville, PA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/385,205

(22) Filed: Dec. 20, 2016

(65) Prior Publication Data

US 2017/0100449 A1    Apr. 13, 2017

Related U.S. Application Data

(63) Continuation of application No. 14/590,143, filed on Jan. 6, 2015, now abandoned, which is a continuation of application No. 13/368,434, filed on Feb. 8, 2012, now abandoned, and a continuation-in-part of application No. PCT/US2012/020863, filed on Jan. 11, 2012.

(60) Provisional application No. 61/431,508, filed on Jan. 11, 2011.

(51) Int. Cl.
| | |
|---|---|
| *A61K 38/05* | (2006.01) |
| *A61K 31/4155* | (2006.01) |
| *A61K 31/69* | (2006.01) |
| *A61K 45/06* | (2006.01) |
| *A61K 38/00* | (2006.01) |
| *A61K 9/00* | (2006.01) |

(52) U.S. Cl.
CPC ............ *A61K 38/05* (2013.01); *A61K 9/0019* (2013.01); *A61K 31/4155* (2013.01); *A61K 31/69* (2013.01); *A61K 38/005* (2013.01); *A61K 45/06* (2013.01)

(58) Field of Classification Search
CPC .................................................... A61K 38/05
USPC .......................................................... 514/64
See application file for complete search history.

(56) References Cited

U.S. PATENT DOCUMENTS

| | | | |
|---|---|---|---|
| 5,604,213 | A | 2/1997 | Barrie et al. |
| 5,681,835 | A | 10/1997 | Willson |
| 5,877,219 | A | 3/1999 | Willson |
| 6,207,716 | B1 | 3/2001 | Willson |
| 6,268,391 | B1 | 7/2001 | Dickerson et al. |
| 6,328,590 | B1 | 12/2001 | Linnell |
| 7,576,209 | B2 | 8/2009 | Kelly, III et al. |
| 7,709,517 | B2 | 5/2010 | Sawyers et al. |
| 2007/0004753 | A1 | 1/2007 | Sawyers et al. |
| 2008/0051380 | A1 | 2/2008 | Auerbach et al. |
| 2008/0053269 | A1 | 3/2008 | Mashiki et al. |
| 2009/0131367 | A1* | 5/2009 | Gore ............... A61K 31/435 514/64 |
| 2009/0163524 | A1 | 6/2009 | Johnson |
| 2010/0035905 | A1 | 2/2010 | Schmidt et al. |
| 2010/0197754 | A1* | 8/2010 | Chen ............... C07D 409/04 514/406 |
| 2013/0018032 | A1 | 1/2013 | Chen |
| 2018/0344699 | A1 | 12/2018 | Kumar |

FOREIGN PATENT DOCUMENTS

| | | |
|---|---|---|
| JP | A 2009-532497 | 9/2009 |
| JP | A-2010-51811 | 3/2010 |
| JP | A 2012-082215 | 4/2012 |
| JP | A 2012-516344 | 7/2012 |
| JP | A 2012-530763 | 12/2012 |
| WO | WO 2006/040649 | 4/2006 |
| WO | WO 2007/113239 | 10/2007 |
| WO | WO 2007/122755 | 11/2007 |
| WO | WO2008070016 | 6/2008 |
| WO | WO2008094321 | 8/2008 |
| WO | WO2008098104 | 8/2008 |
| WO | WO 2010/088331 | 8/2010 |
| WO | WO 2010/149755 | 12/2010 |
| WO | WO 2011/044415 | 4/2011 |
| WO | WO 2012/135750 | 10/2012 |
| WO | WO 2012/135759 | 10/2012 |
| WO | WO 2012/151413 | 11/2012 |
| WO | WO 2013/053691 | 4/2013 |
| WO | WO 2013/079964 | 6/2013 |
| WO | WO 2013/184572 | 12/2013 |

OTHER PUBLICATIONS

Mitsiades et al. Semin. Hematol. (2009), pp. 166-175 (Year: 2009).*
Vogelstein et al. Nature Medicine (2004), vol. 10, pp. 789-799 (Year: 2004).*
Hideshima et al. Perifosine, an oral bioactive novel alkylphospholipid, inhibits Akt and induces in vitro and in vivo cytotoxicity in human multiple myeloma cells. Blood (2006) vol. 107, pp. 4053-4062.
Adams, et al., Cancer Invest, 22(2):301-311 (2004 ).
Adams, et al., Science, 281:1322-1326 (1998).
Alessi, et al., EMBO J., 15:6541-6551 (1996).
Bellacosa, et al., Int. J. Cancer, 64:280-285 (1995).
Bouma, et al., J. Antimicrob. Chemother., 42(6):817-820 (1998).
Crews, et al., Cell, 74:215-217 (1993).
Downward, Curr. Opin. Cell Biology, 10:262-267 (1998).
Dudek, et al., Science, 275:661-665 (1997).
Feling, et al., Angew. Chem. Int. Ed. Engl., 42(3):355-7 (2003).
Franke, et al., Cell, 81:727-736 (1995).
Franke, et al., Cell, 88:435-437 (1997).

(Continued)

*Primary Examiner* — Melenie L Gordon
*Assistant Examiner* — Taina D Matos Negron
(74) *Attorney, Agent, or Firm* — Fish & Richardson P.C.

(57) ABSTRACT

The present invention relates to a method of treating cancer in a human and to pharmaceutical combinations useful in such treatment. In particular, the method relates to a cancer treatment method that includes administering a proteasome inhibiting compound, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt thereof, and optional additional antineoplastic agents, to a human in need thereof.

2 Claims, 3 Drawing Sheets

(56) References Cited

OTHER PUBLICATIONS

Gills, et al., Current Oncology Reports, Perifosine, 11:102-110 (2009).
Guldberg et al. Cancer Research 57:3660-3663 (1997).
Hemmings, et al., Science, 275:628-630 (1997).
Hemmings, Science, 277:534 (1997).
J. Q. Cheung, et al., Proc. Natl. Acad. Sci. USA, 89:9267-9271 (1992).
J. Q. Cheung, et al., Proc. Natl. Acad. Sci. USA, 93:3636-3641 (1996).
Kauffmann-Zeh, et al., Nature, 385:544-548 (1997).
Kuhn, et al., Blood, 110:3281-3290 (2007).
Kulik, et al., Mel. Cellular Biology, 17:1595-1601 (1997).
Landis-Piwowar, et al., Drug Resistance Updates, 9(6):263-273 (2007).
Li et al. Science 275:1943-1947 (1997).
Liaw et al. Nature Genetics 16:64-67 (1997).
Nakatani, et al., J. Biol. Chem., 274:21528-21532 (1999).
Richardson, et al., Blood, 11 O:Abstract 1170 (2007), XP-002723815.
Risinger et al. Cancer Research 57:4736-4738 (1997).
Silberman, Jeannine, et al., Blood, 11 0(11 ):2758 (2007), XP0081 02628.
Stambolic et al. Cell 95:29-39 (1998).
Sun et al. Proc. Natl. Acad. Sci. U.S.A. 96:6199-6204 (1999).
Sun et al. Am. J. Pathol. 159:431-7 (2001).
Thomberry, et al., Science, 281:1312-1316 (1998).
Veerandra Munugalavadal, et al., Blood, 114:3788 (2009), XP-002723816.
Williamson, et al., The Journal of Allergy and Clinical Immunology, 118(6):1369-74 (2006).
EP Search Report dated 14.05.14, EP App. No. 12733916.6.
Akintunde Akinleye et al., "Ibrutinib and novel BTK inhibitors in clinical development", Journal of Hematology & Oncology, Biomed Central Ltd, London UK., vol. 6, No. 1, p. 59, Aug. 19, 2013.
Ayala et al., "Bortezomib-Mediated inhibition of Steroid Receptor Coactivator-3Degradation Leads to Activated Akt.", Clin. Cancer Research, 14(22), pp. 7511-7518, 2008.
Brekken et al., "Selective inhibition of vascular endothelial growth factor (VEGF) receptor 2 (KDR/FLK-1) activity by a monoclonal anti-VEGF antibody blocks tumor growth in mice.", Cancer Res., 60, 5117-5124, 2000.
Fantin et al., "Attenuation of LDH—A expression uncovers a link between glycolysis, mitochondrial physiology, and tumor maintenance.", Cancer Cell, 9, 425, 2006.
Gottlicher et al., "Valproic acid defines a novel class of HDAC inhibitors inducing differentiation of transformed cells.", EMBO J. 20(24): 6969-6978, 2001.
Griner et al, "High-throughput combinatorial screening identifies drugs that cooperate with ibruinib to kill activated B-cell-like diffuse large B-cell lymphoma cells", PNAS, vol. 111, No. 6, pp. 2349-2354, 2014.
Japanese Office Action in Japanese Application No. 2013-549503, dated Dec. 18, 2015, 3 pages.
Japanese Office Action in Japanese Application No. 2016-556821, dated Oct. 30, 2018.
Jia Wet al., "Synergistic antileukemic interactions between 17-AAG and UCN-01 involve interruption of RAF/MEK- and AKT-related pathways.", Blood., 102(5): 1824-32, 2003.
"Markman et al., ""Taxol: an important new drug in the management of epithelial ovarian cancer."", Yale Journal of Biology and Medicine, 64: 583-590, 1991".
Martinez-Lacaci et al., "RAS transformation causes sustained activation of epidermal growth factor receptor and elevation of mitogen-activated protein kinase in human mammary epithelial cells.", Int. J. Cancer, 88(1), 44-52, 2000.
Richon et al., "Histone deacetylase inhibitor selectively induces p21WAF1 expression and gene-associated histone acetylation.", Proc. Nat Acad. Sci. U.S.A. 97(18): 10014-10019, 2000.
Stern, Tyrosine kinase signalling in breast cancer: ErbB family receptor tyrosine kinases, Breast cancer Res., 2(3), 176-183, 2000.
Yamamoto et al., "Ras-induced transformation and signaling pathway.", Journal of Biochemistry. 126 (5) 799-803, 1999.
Zhong et al., "Modulation of hypoxia-inducible factor lalpha expression by the epidermal growth factor/phosphatidylinositol 3 kinase/PTEN/AKT/FRAP pathway in human prostate cancer cells: implications for tumor angiogenesis and therapeutics.", Cancer res, 60(6), 1541-1545, 2000.
Abraham, "Phosphatidylinositol 3-kinase related kinases.", Current Opinion in Immunology. 8 (3) 412-8, 1996.
Ahlneck et al., "The molecular basis of moisture effects on the physical and chemical stability of drugs in the solid state", Int J Pharm, 62(2-3): 87-95, 1990.
Ashby, "CaaX converting enzymes.", Current Opinion in Lipidology. 9 (2) 99-102, 1998.
Balasubramanian et al., "Isoform-specific histone deacetylase inhibitors: the next step?", Cancer Letters 280: 211-221, 2009.
Ball et al., "p21: structure and functions associated with cyclin-CDK binding.", Progress in Cell Cycle Res., 3: 125, 1997.
Berenbaum, "Criteria for Analyzing Interactions between Biologically Active Agents", MC Adv. Cancer Research, 35, 269-335, 1981.
Bertrand, "Inside HDAC with HDAC inhibitors.", European Journal of Medicinal Chemistry 45, 2095-2116, 2010.
Bhutani et al., "AKT inhibitors: mechanism of action and implications for anticancer therapeutics", Infectious Agents and Cancer, vol. 8, No. 1, p. 49, Dec. 13, 2013.
Bolen et al., "Leukocyte protein tyrosine kinases: potential targets for drug discovery.", Annual review of Immunology. 15: 371-404, 1997.
Brawer et al., "New Treatments for Castration-Resistant Prostate Cancer", Rev Urol 10 (4): 294-296, 2008.
Brodt et al., "Inhibition of the type I insulin-like growth factor receptor expression and signaling: novel strategies for antimetastatic therapy.", Biochemical Pharmacology, 60, 1101-1107, 2000.
Byrn et al., "Pharmaceutical Solids: a strategic approach to regulatory Considerations," Pharma Res, 1995, 12(7): 945-954.
Canman et al., "The role of ATM in DNA damage responses and cancer", Oncogene 17 (25) 3301-3308, 1998.
Cayman Chemical. MDV3100. Electronic Resource: [https://www.caymanchem.com/product/11596].
"Chou and Talalay, ""Quantitative Analysis of Dose-Effect Relationships: The Combined Effects of Multiple Drugs or Enzyme Inhibitors""", Advances in Enzyme Regulation, 22, 37-55, 1984".
Davies et al., Preclinical pharmacology of AZD5363, an inhibitor of AKT: pharmacodynamics, antitumor activity, and Correlation of monotherapy activity with genetic backgroundn, Mol. Cancer Ther_ vol. 11, No. 4, pp. 873-887, 2012.
Dayyani et al., "Novel Therapies for Metastatic Castrate-Resistant Prostate Cancer", JNCI Journal of the National Cancer Institute, vol. 103, No. 22, pp. 1665-1675, 2011.
European Journal of Cancer, p. 112-113, vol. 48, supplement6, Poster-Session PB kinase '368', Nov. 2, 2012.
Green et al., "Monoclonal Antibody Therapy for Solid Tumors", Cancer Treat. Rev., 26(4), 269-286, 2000.
Guardabassi et al., "Retrospective detection of methicillin resistant and susceptible Staphylococcus aureus ST398 in Danish slaughter pigs.", Community Oncology 4, 384-386, 2007.
Hancock et al., "Characteristics and Significance of the Amorphous State in Pharmaceutical Systems", J Pharm Sci, 86(1): 1-12, 1997.
Holmes et al., "Phase II trial of taxol, an active drug in the treatment of metastatic breast cancer.", J. Nat. Cancer Inst., 83: 1797-1805, 1991.
Jackson, "DNA-dependent protein kinase.", International Journal of Biochemistry and Cell Biology. 29 (7): 935-8, 1997.
Japanese Office Action in Application No. 2016-519395, dated Apr. 4, 2019, English Translation, 1 page.
Japanese Office Action in Application No. 2018-040124, dated Apr. 3, 2019, English Translation, 1 page.
JP Office Action in Japanese Appln. No. 2016-235681, dated Oct. 2, 2018, 5 pages.

(56) References Cited

OTHER PUBLICATIONS

Kath, "Patent focus: inhibitors of tumour cell growth", John C., Exp. Opin. Ther. Patents, 10(6): 803-818, 2000.
Kearns et al., "Paclitaxel pharmacokinetics and pharmacodynamics.", Seminars in Oncology, 3(6) p. 16-23, 1995.
Kirshenbaum et al., "Targeting Androgen Receptor-Dependent Prostate Cancer With Multivalent Ethfsterone Conjugates", The Journal of Urology, May 2013, vol. 189, No. 4S, Supplement, p. e402.
Lackey et al., "The discovery of potent cRaf1 kinase inhibitors.", Bioorganic and Medicinal Chemistry Letters, (10), 223-226, 2000.
Lee et al., "Radicicol represses the transcriptional function of the estrogen receptor by suppressing the stabilization of the receptor by heat shock protein 90.", Mol Cell Endocrinol., 188,47-54, 2002.
Li et al., "PTEN, a putative protein tyrosine phosphatase gene mutated in human brain, breast, and prostate cancer.", Science 275: 1943-1947, 1997.
Lin et al., "Suppression Versus Induction of Androgen Receptor Functions by the Phosphatidylinositol 3•Kinase/Akt Pathway in Prostate Cancer LNCaP Cells with Different Passage Numbers the Journal of Biological Chemistry", vol. 278, No. 51, p. 50902-50907, 2003.
Liu et al., "PAP: Detection of Ultra Rare Mutations Depends on Pn Oligonucleotides: "Sleeping Beauties" Awakened by the Kiss of Pyrophosphorolysis", Human Mutation 23: 426-436, 2004.
Marks et al., "Dimethyl sulfoxide to vorinostat: development of this histone deacetylase inhibitor as an anticancer drug.", Nature Biotechnology 25, 84-90, 2007.
Massague et al., "Serine/threonine kinase receptors: mediators of transforming growth factor beta family signals", Cancer Surveys. 27:41-64, 1996.
McGuire et al., "Taxol: a unique antineoplastic agent with significant activity in advanced ovarian epithelial neoplasms.", Ann. Intern, Med., 111: 273-279, 1989.
O'Donnell et al., "Hormonal impact of the 17α-hydroxylase/C17,20-lyase inhibitor abiraterone acetate (CB7630) in patients with prostate cancer", British Journal of Cancer, 90: 2317-2325, 2004.
Oliff, "Farnesyltransferase inhibitors: targeting the molecular basis of cancer.", BioChim. Biophys. Acta, 1423(3): 19-30, 1999.
Philip et al., "Potential for protein kinase C inhibitors in cancer therapy.", Cancer Treatment and Research. 78: 3-27, 1995.
Rathkopf et al., "Phase I study of ARN-509, a novel antiandrogen, in the treatment of castration-resistant prostate cancer.", J Clin Oncol., 31 (28): 3525-30, 2013.
Revill et al., "Drugs of the Future", 32(4): 315-322, 2007.
Rhodes et al., "Characterization of an AKT kinase inhibitor with potent pharmacodynamic and antitumor activity.", Cancer Res., 68: 2366-74, 2008.
Rosania et al., "Targeting hyperproliferative disorders with cyclin dependent kinase inhibitors", Exp. Opin. Ther. Patents, 10(2): 215-230, 2000.
Samuels et al., "Oncogenic P13K and its role in cancer.", Current Opinion in Oncology, 18:77-82, 2006.
Scharovsky et al., "Inhibition of ras oncogene: a novel approach to antineoplastic therapy.", Journal of Biomedical Science. 7(4) 292-8, 2000.
Shawver et al., "Receptor tyrosine kinases as targets for inhibition of angiogenesis", DDT vol. 2, No. 2 Feb. 1997.
Singh et al., "Molecular and traditional chemotherapy: a united front against prostate cancer.", Cancer Lett., 293: 1-14, 2010.
Sinh, S. and Corey, S.J., "Implications for SRC kinases in hematopoiesis: signal transduction therapeutics.", Journal of Hematotherapy and Stem Cell Research 8 (5): 465-80, 1999.
Smithgall, "SH2 and SH3 domains: potential targets for anti-cancer drug design.", Journal of Pharmacological and Toxicological Methods. 34(3) 125-32, 1995.
Spencer et al., "Novel AKT Inhibitor GSK2110183 Shows Favorable Safety, Pharmacokinetics, and Clinical Activity in Multiple Myeloma. Preliminary Results From a Phase I First-Time-In-Human Study", Blood, vol. 118, No. 21, Abstract 1856, p. 808, Nov. 2011.
Tennant et al., "Targeting metabolic transformation for cancer therapy.", Nature Reviews, (4): 267-277, 2010.
Toren et al., "Combined Targeting of P13K/AKT and AR Pathway With AZD5363 and Ezalutamide Induces Anticancer Activity in Preclinical Models of Prostate Cancer", The Journal of Urology, May 2013, vol. 189, No. 4S, Supplement, p. e403, 982, May 6, 2013.
Tran et al., Development of a Second-Generation Antiandrogen for Treatment of Advanced Prostate CancerScience, vol. 324, p. 787-790, 2009.
Tyle, "Iontophoretic Devices for Drug Delivery.", Pharmaceutical Research, 3(6), 318-326, 1986.
Vigushin et al., "Histone deacetylase inhibitors in cancer treatment.", Anticancer Drugs, 13(1): 1-13, 2002.
Vinodhkumar et al., "Romidepsin (depsipeptide) induced cell cycle arrest, apoptosis and histone hyperacetylation in lung carcinoma cells (A549) are associated with increase in p21 and hypophosphorylated retinoblastoma proteins expression.", Biomedicine & Pharmacotherapy 62, 85-93, 2008.
Woo et al., "Taxol inhibits progression of congenital polycystic kidney disease.", Nature, 368: 750-753, 1994.
Yin et al., "Recent Progress in Pharmaceutical Therapies for Castration-Resistant Prostate Cancer", International Journal of Molecular Sciences, vol. 14, No. 7, pp. 13958-13978, Jul. 4, 2013.
Yu et al., "Anti-androgens and androgen-depleting therapies in prostate cancer: new agents for an established target.", LancetOncol., 10: 981-91, 2009.

* cited by examiner

COMBINATION

This application is a continuation of U.S. application Ser. No. 14/590,143, filed Jan. 6, 2015, which is a continuation of U.S. application Ser. No. 13/368,434, filed Feb. 8, 2012, which is a Continuation-in-Part of International Application No. PCT/US2012/020863 filed Jan. 11, 2012, which claims priority from U.S. Provisional Application No. 61/431,508 filed Jan. 11, 2011.

FIELD OF THE INVENTION

The present invention relates to a method of treating cancer in a mammal and to combinations useful in such treatment. In particular, the method relates to a novel combination comprising a proteasome inhibiting compound, and the Akt inhibitor: N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt thereof, and optional additional antineoplastic agents; pharmaceutical compositions comprising the same; and methods of using such combinations in the treatment of cancer.

BACKGROUND OF THE INVENTION

Generally, cancer results from the deregulation of the normal processes that control cell division, differentiation and apoptotic cell death. Apoptosis (programmed cell death) plays essential roles in embryonic development and pathogenesis of various diseases, such as degenerative neuronal diseases, cardiovascular diseases and cancer. One of the most commonly studied pathways, which involves kinase regulation of apoptosis, is cellular signaling from growth factor receptors at the cell surface to the nucleus (Crews and Erikson, Cell, 74:215-17, 1993).

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science,* 281:1322-1326 (1998)). The execution of programmed cell death is mediated by caspase-1 related proteinases, including caspase-3, caspase-7, caspase-8 and caspase-9 etc (Thornberry et al. *Science,* 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell,* 88:435-437 (1997); Kauffmann-Zeh et al. *Nature* 385:544-548 (1997) Hemmings *Science,* 275:628-630 (1997); Dudek et al., *Science,* 275:661-665 (1997)). Survival factors, such as platelet derived growth factor (PDGF), nerve growth factor (NGF) and insulin-like growth factor-1 (IGF-I), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell,* 81:727-736 (1995); Hemmings *Science,* 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was overexpressed in 12% of ovarian carcinomas and that amplification of Akt was especially frequent in 50% of undifferentiated tumors, suggesting that Akt may also be associated with tumor aggressiveness (Bellacosa, et al., *Int. J. Cancer,* 64, pp. 280-285, 1995). Increased Akt1 kinase activity has been reported in breast, ovarian and prostate cancers (Sun et al. *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis and/or cancer.

Proteasome inhibitors are drugs that block the action of proteasomes, cellular complexes that break down proteins, like the p53 protein. Several proteasome inhibitors are marketed or are being studied in the treatment of cancer.

It would be useful to provide a novel therapy which provides more effective and/or enhanced treatment of an individual suffering the effects of cancer.

SUMMARY OF THE INVENTION

One embodiment of this invention provides a combination comprising:
(i) a proteasome inhibiting compound;
(ii) a compound of Structure (II):

or a pharmaceutically acceptable salt thereof; and
(iii) optional additional antineoplastic agents.

One embodiment of this invention provides a combination comprising:
(i) a proteasome inhibiting compound; and
(ii) a compound of Structure (II):

or a pharmaceutically acceptable salt thereof.

One embodiment of this invention provides a combination comprising:
(i) a compound of Structure (I):

or a pharmaceutically acceptable salt thereof;
(ii) a compound of Structure (II):

or a pharmaceutically acceptable salt thereof; and
(iii) optional additional antineoplastic agents.

One embodiment of this invention provides a combination comprising:
(i) a compound of Structure (I):

or a pharmaceutically acceptable salt thereof;

(ii) a compound of Structure (II):

or a pharmaceutically acceptable salt thereof.

One embodiment of this invention provides a method of treating cancer in a human in need thereof which comprises the in vivo administration of a therapeutically effective amount of a combination of a proteasome inhibiting compound, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, and optional additional antineoplastic agents, to such human.

One embodiment of this invention provides a method of treating cancer in a human in need thereof which comprises the in vivo administration of a therapeutically effective amount of a combination of a proteasome inhibiting compound, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, to such human,
wherein the combination is administered within a specified period, and
wherein the combination is administered for a duration of time.

One embodiment of this invention provides a method of treating cancer in a human in need thereof which comprises the in vivo administration of a therapeutically effective amount of a combination of a proteasome inhibiting compound, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, to such human,
wherein the compounds of the combination are administered sequentially.

DETAILED DESCRIPTION OF THE INVENTION

The present invention relates to combinations that exhibit antiproliferative activity. Suitably, the method relates to methods of treating cancer by the co-administration of a proteasome inhibiting compound, suitably bortezomib (Velcade®), (hereinafter Compound A, or a pharmaceutically acceptable salt thereof, which compound is represented by Structure I:

and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, (hereinafter Compound B or a pharmaceutically acceptable salt, suitably the hydrochloride salt, thereof, which compound is represented by Structure II:

Compound A is sold commercially for the treatment of cancer. Compound A is known by the generic name bortezomib and the trade name Velcade®.

Compound B is disclosed and claimed, along with pharmaceutically acceptable salts thereof, as being useful as an inhibitor of AKT activity, particularly in treatment of cancer, in International Application No. PCT/US2008/053269, having an International filing date of Feb. 7, 2008; International Publication Number WO 2008/098104 and an International Publication date of Aug. 14, 2008, the entire disclosure of which is hereby incorporated by reference, Compound B is the compound of example 96. Compound B can be prepared as described in International Application No. PCT/US2008/053269.

Suitably, Compound B is in the form of a hydrochloride salt. The salt form can be prepared by one of skill in the art from the description in United States Patent Application Publication: US 2010/0197754 A1, filed 28 Jan. 2010, having a publication date of Aug. 5, 2010.

As used herein the term "Compound C" means N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride.

The administration of a therapeutically effective amount of the combinations of the invention are advantageous over the individual component compounds in that the combinations provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

The compounds of the invention may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of proteasome inhibiting compounds, suitably Compound A, and pharmaceutically acceptable salts thereof, and Compound B, and pharmaceutically acceptable salts thereof and optional additional antineoplastic agents.

The compounds of the invention may form a solvate which is understood to be a complex of variable stoichiometry formed by a solute (in this invention, Compound A or a salt thereof and/or Compound B or a salt thereof and optional additional antineoplastic agents) and a solvent. Such solvents for the purpose of the invention may not interfere with the biological activity of the solute. Examples of suitable solvents include, but are not limited to, water, methanol, ethanol and acetic acid. Suitably the solvent used is a pharmaceutically acceptable solvent. Suitably the solvent used is water.

The pharmaceutically acceptable salts of the compounds of the invention are readily prepared by those of skill in the art.

Also, contemplated herein is a method of treating cancer using a combination of the invention where Compound A, or a pharmaceutically acceptable salt thereof, and/or Compound B or a pharmaceutically acceptable salt thereof or optional additional antineoplastic agents are administered as pro-drugs. Pharmaceutically acceptable pro-drugs of the compounds of the invention are readily prepared by those of skill in the art.

When referring to a dosing protocol, the term "day", "per day" and the like, refer to a time within one calendar day which begins at midnight and ends at the following midnight.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent or combination that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "combination" and derivatives thereof, unless otherwise defined, is meant either, simultaneous administration or any manner of separate sequential administration of a therapeutically effective amount of Compound A, or a pharmaceutically acceptable salt thereof, and Compound B or a pharmaceutically acceptable salt thereof and optional additional antineoplastic agents. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, both compounds are administered orally. Suitably Compound A is administered intravenously and Compound B is administered orally.

By the term "combination kit" as used herein is meant the pharmaceutical composition or compositions that are used to administer Compound A, or a pharmaceutically acceptable salt thereof, and Compound B, or a pharmaceutically acceptable salt thereof and optional additional antineoplastic agents, according to the invention. When two compounds are administered simultaneously, the combination kit can contain Compound A, or a pharmaceutically acceptable salt thereof, and Compound B, or a pharmaceutically acceptable salt thereof, in a single pharmaceutical composition, such as a tablet, or in separate pharmaceutical compositions. When the compounds are not administered simultaneously, the combination kit will contain Compound A, or a pharmaceutically acceptable salt thereof, and Compound B, or a pharmaceutically acceptable salt thereof, and optional additional antineoplastic agents, in separate pharmaceutical compositions. The combination kit can comprise Compound A, or a pharmaceutically acceptable salt thereof, and Compound B, or a pharmaceutically acceptable salt thereof, in separate pharmaceutical compositions in a single package or in separate pharmaceutical compositions in separate packages.

In one aspect there is provided a combination kit comprising the components:

Compound A, or a pharmaceutically acceptable salt thereof, in association with a pharmaceutically acceptable carrier; and Compound B, or a pharmaceutically acceptable salt thereof, in association with a pharmaceutically acceptable carrier.

In one embodiment of the invention the combination kit comprises the following components:

Compound A, or a pharmaceutically acceptable salt thereof, in association with a pharmaceutically acceptable carrier; and Compound B, or a pharmaceutically acceptable salt thereof, in association with a pharmaceutically acceptable carrier, wherein the components are provided in a form which is suitable for sequential, separate and/or simultaneous administration.

In one embodiment the combination kit comprises:

a first container comprising Compound A, or a pharmaceutically acceptable salt thereof, in association with a pharmaceutically acceptable carrier; and a second container comprising Compound B, or a pharmaceutically acceptable salt thereof, in association with a pharmaceutically acceptable carrier, and a container means for containing said first and second containers.

The "combination kit" can also be provided by instruction, such as dosage and administration instructions. Such dosage and administration instructions can be of the kind that is provided to a doctor, for example by a drug product label, or they can be of the kind that is provided by a doctor, such as instructions to a patient.

As used herein the term "Compound A$^2$" means—Compound A, or a pharmaceutically acceptable salt thereof or another proteasome inhibitor as defined herein, suitably Compound A—.

As used herein the term "Compound B$^2$" means—Compound B, or a pharmaceutically acceptable salt thereof—.

In one embodiment of the present invention Compound B is replaced by:

8-[4-(1-aminocyclobutyl)phenyl]-9-phenyl[1,2,4]triazolo[3,4-f]-1,6-naphthyridin-3(2H)-one: which has the following structure (depicted as the chloride salt):

In one embodiment of the present invention Compound B$^2$ is replaced by:

8-[4-(1-aminocyclobutyl)phenyl]-9-phenyl[1,2,4]triazolo[3,4-f]-1,6-naphthyridin-3(2H)-one or a pharmaceutically acceptable salt thereof.

The compound 8-[4-(1-aminocyclobutyl)phenyl]-9-phenyl[1,2,4]triazolo[3,4-f]-1,6-naphthyridin-3(2H)-one is disclosed and claimed, along with pharmaceutically acceptable salts thereof, as being useful as an inhibitor of AKT activity, particularly in treatment of cancer, in U.S. Pat. No. 7,576,209 which issued on Aug. 18, 2009. 8-[4-(1-aminocyclobutyl)phenyl]-9-phenyl[1,2,4]triazolo[3,4-f]-1,6-naphthyridin-3(2H)-one can be prepared as described in U.S. Pat. No. 7,576,209.

By the term "proteasome inhibiting compound", "proteasome inhibitors" and derivatives thereof, as used herein, unless otherwise defined, is meant the class of compounds that block the action of proteasomes, cellular complexes that break down proteins, like the p53 protein. Several proteasome inhibitors are marketed or are being studied in the treatment of cancer. Suitable proteasome inhibitors for use herein include:

1. Bortezomib (Velcade®), including pharmaceutically acceptable salts thereof. Adams J, Kauffman M (2004), *Cancer Invest* 22 (2): 304-11.

Bortezomib has the following chemical structure and name.

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof.
Bouma et al. (1998). *J. Antimicrob. Chemother.* 42 (6): 817-20.
Disulfiram has the following chemical structure and name.

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), *The Journal of Allergy and Clinical Immunology* 118 (6): 1369-74.
Epigallocatechin gallate has the following chemical structure and name.

[(2R,3R)-5,7-dihydroxy-2-(3,4,5-trihydroxyphenyl)chroman-3-yl]3,4,5-trihydroxybenzoate

4. Salinosporamide A, including pharmaceutically acceptable salts thereof. Feling et at., (2003), *Angew. Chem. Int. Ed. Engl.* 42 (3): 355-7.

Salinosporamide A has the following chemical structure and name.

(4R,5S)-4-(2-chloroethyl)-1-((1S)-cyclohex-2-enyl(hydroxy)methyl)-5-methyl-6-oxa-2-azabicyclo3.2.0heptane-3,7-dione 5. Carfilzomib, including pharmaceutically acceptable salts thereof.
Kuhn D J, et al, Blood, 2007, 110:3281-3290.
Carfilzomib has the following chemical structure and name.

(aS)-a-[(4-morpholinylacetyl)amino]benzenebutanoyl-L-leucyl-N-[(1S)-3-methyl-1-[[(2R)-2-methyloxiranyl]carbonyl]butyl]-L-Phenylalaninamide By the term "additional antineoplastic agent(s)" and derivatives thereof, as used herein, unless otherwise defined, is meant further compounds known to treat cancer or to be useful when administered with a compound or compounds that are known to treat cancer. Suitably, additional antineoplastic agents for use herein include: gemcitabine, carboplatin, cisplatin, cytarabine, thalidomide, Revlimid® (lenalidomide), decitabine, melphalan (Alkeran), cyclophosphamide (Cytoxan), vincristine (Oncovin), doxorubicin (Adriamycin), liposomal doxorubicin (Doxil), prednisone, dexamethasone (Decadron) and eltrombopag (Promacta®). Suitably, the additional antineoplastic agent is an agent useful in the treatment of multiple myeloma.

By the term "specified period", as used herein is meant the interval of time between the administration of one of Compound $A^2$ and Compound $B^2$ and the other of Compound $A^2$ and Compound $B^2$. Unless otherwise defined, the specified period can include simultaneous administration. When both compounds of the invention are administered once a day the specified period refers to timing of the administration of Compound $A^2$ and Compound $B^2$ during a single day. When one or both compounds of the invention are administered more than once a day, the specified period is calculated based on the first administration of each compound on a specific day. All administrations of a compound of the invention that are subsequent to the first during a specific day are not considered when calculating the specific period.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other in this case, the specified period will be about 4 hours; suitably they will both be administered within about 3 hours of each other—in this case, the specified period will be about 3 hours; suitably they will be administered within about 2 hours of each other—in this case, the specified period will be about 2 hours; suitably they will both be administered within about 1 hour of each other—in this case, the specified period will be about 1 hour. As used herein, the administration of Compound $A^2$ and Compound $B^2$ in less than about 45 minutes apart is considered simultaneous administration.

Suitably, when the combination of the invention is administered for a "specified period", the compounds will be co-administered for a "duration of time".

By the term "duration of time" and derivatives thereof, as used herein is meant that both compounds of the invention are administered within a "specified period" for an indicated number of consecutive days, optionally followed by a number of consecutive days where only one of the component compounds is administered. Unless otherwise defined, the "duration of time" and in all dosing protocols described herein, do not have to commence with the start of treatment and terminate with the end of treatment, it is only required that the number of consecutive days in which both compounds are administered and the optional number of consecutive days in which only one of the component compounds is administered, or the indicated dosing protocol, occur at some point during the course of treatment.

Regarding "specified period" administration:

Suitably, during the course of treatment, both compounds will be administered within a specified period for at least 1 day—in this case, the duration of time will be at least 1 day; suitably, during the course of treatment, both compounds will be administered within a specified period for at least 2 consecutive days—in this case, the duration of time will be at least 2 days; suitably, during the course of treatment, both compounds will be administered within a specified period for at least 3 consecutive days—in this case, the duration of time will be at least 3 days; suitably, during the course of treatment, both compounds will be administered within a specified period for at least 5 consecutive days—in this case, the duration of time will be at least 5 days; suitably, during the course of treatment, both compounds will be administered within a specified period for at least 7 consecutive days—in this case, the duration of time will be at least 7 days; suitably, during the course of treatment, both compounds will be administered within a specified period for at least 14 consecutive days—in this case, the duration of time will be at least 14 days; suitably, during the course of treatment, both compounds will be administered within a specified period for at least 30 consecutive days—in this case, the duration of time will be at least 30 days. When, during the course of treatment, both compounds are administered within a specified period for over 30 days, the treatment is considered chronic treatment and will continue until an altering event, such as a reassessment in cancer status or a change in the condition of the patient, warrants a modification to the protocol.

Further regarding "specified period" administration:

Suitably, during the course of treatment, both compounds will be administered within a specified period for at least 1 day, followed by the administration of Compound $A^2$ alone for at least 1 day—in this case, the duration of time will be at least 2 days; suitably, during the course of treatment, both compounds will be administered within a specified period for at least 1 day, followed by administration of Compound $A^2$ alone for at least 2 days—in this case, the duration of time will be at least 3 days; suitably, during the course of treatment, both compounds will be administered within a specified period for at least 1 day, followed by administration of Compound $A^2$ alone for at least 3 days—in this case, the duration of time will be at least 4 days; suitably, during the course of treatment, both compounds will be administered within a specified period for at least 1 day, followed by administration of Compound $A^2$ alone for at least 4 days—in this case, the duration of time will be at least 5 days; suitably, during the course of treatment, both compounds will be administered within a specified period for at least 1 day, followed by administration of Compound $A^2$ alone for at least 5 days—in this case, the duration of time will be at least 6 days; suitably, during the course of treatment, both compounds will be administered within a specified period for at least 1 day, followed by administration of Compound $A^2$ alone for at least 6 days—in this case, the duration of time will be at least 7 days; suitably, during the course of treatment, both compounds will be administered within a specified period for at least 1 day, followed by administration of Compound $A^2$ alone for at least 7 days—in this case, the duration of time will be at least 8 days; suitably, during the course of treatment, both compounds will be administered within a specified period for at least 2 consecutive days, followed by administration of Compound $A^2$ alone for at least 1 day—in this case, the duration of time will be at least 3 days; suitably, during the course of treatment, both compounds will be administered within a specified period for at least 2 consecutive days, followed by administration of Compound $A^2$ alone for at least 2 consecutive days—in this case, the duration of time will be at least 4 days; suitably, during the course of treatment, both compounds will be administered within a specified period for at least 2 consecutive days, followed by administration of Compound $A^2$ alone for at least 3 consecutive days—in this case, the duration of time will be at least 5 days; suitably, during the course of treatment, both compounds will be administered within a specified period for at least 2 consecutive days, followed by administration of Compound $A^2$ alone for at least 4 consecutive days—in this case, the duration of time will be at least 6 days; suitably, during the course of treatment, both compounds will be administered within a specified period for at least 2 consecutive days, followed by administration of Compound $A^2$ alone for at least 5 consecutive days—in this case, the duration of time will be at least 7 days; suitably, during the course of treatment, both compounds will be administered within a specified period for at least 2 consecutive days, followed by administration of Compound $A^2$ alone for at least 6 consecutive days—in this case, the duration of time will be at least 8 days; suitably, during the course of treatment, both compounds will be administered within a specified period for at least 2 consecutive days, followed by administration of Compound $A^2$ alone for at least 7 consecutive days—in this case, the duration of time will be at least 9 days; suitably, during the course of treatment, both compounds will be administered within a specified period for at least 3 consecutive days, followed by administration of Compound $A^2$ alone for at least 1 day—in this case, the duration of time will be at least 4 days; suitably, during the course of treatment, both compounds will be administered within a specified period for at least 3 consecutive days, followed by administration of Compound $A^2$ alone for at least 2 consecutive days—in this case, the duration of time will be at least 5 days; suitably, during the course of treatment, both compounds will be administered within a specified period for at least 3 consecutive days, followed by administration of Compound $A^2$ alone for at least 3 consecutive days—in this case, the duration of time will be at least 6 days; suitably, during the course of treatment, both compounds will be administered within a specified period for at least 3 consecutive days, followed by administration of Compound $A^2$ alone for at least 4 consecutive days—in this case, the duration of time will be at least 7 days; suitably, during the course of treatment, both compounds will be administered within a specified period for at least 3 consecutive days, followed by administration of Compound $A^2$ alone for at least 5 consecutive days—in this case, the duration of time will be at least 8 days; suitably, during the course of treatment, both compounds will be administered within a specified period for at least 3 consecutive days, followed by administration of Compound $A^2$ alone for at least 6 consecutive days—in this case, the duration of time will be at least 9 days; suitably, during the course of treatment, both compounds will be administered within a specified period for at least 3 consecutive days, followed by administration of Compound $A^2$ alone for at least 7 consecutive days—in this case, the duration of time will be at least 10 days; suitably, during the course of treatment, both compounds will be administered within a specified period for at least 4 consecutive days, followed by administration of Compound $A^2$ alone for at least 1 day—in this case, the duration of time will be at least 5 consecutive days; suitably, during the course of treatment, both compounds will be administered within a specified period for at least 4 consecutive days, followed by administration of Compound $A^2$ alone for at least 2 consecutive days—in this case, the duration of time will be at least 6 consecutive days; suitably, during the course of treatment, both compounds will be administered within a specified period for at least 4 consecutive days, followed by administration of Compound $A^2$ alone for at least 3 consecutive days—in this case, the duration of time will be at least 7 consecutive days; suitably, during the course of treatment, both compounds will be administered within a specified period for at least 4 consecutive days, followed by administration of Compound $A^2$ alone for at least 4 consecutive days—in this case, the duration of time will be at least 8 consecutive days; suitably, during the course of treatment, both compounds will be administered within a specified period for at least 4 consecutive days, followed by administration of Compound $A^2$ alone for at least 7 consecutive days—in this case, the duration of time will be at least 11 consecutive days; suitably, during the course of treatment, both compounds will be administered within a specified period for at least 5 consecutive days, followed by administration of Compound $A^2$ alone for at least 1 day—in this case, the duration of time will be at least 6 consecutive days; suitably, during the course of treatment, both compounds will be administered within a specified period for at least 5 consecutive days, followed by administration of Compound $A^2$ alone for at least 2 consecutive days—in this case, the duration of time will be at least 7 consecutive days; suitably, during the course of treatment, both compounds will be administered within a specified period for at least 5 consecutive days, followed by administration of Compound $A^2$ alone for at least 3 consecutive days—in this case, the duration of time will be at least 8 consecutive days; suitably, during the course of treatment, both compounds will be administered within a specified period for at least 5 consecutive days, followed by administration of Compound $A^2$ alone for at least 4 consecutive days—in this case, the duration of time will be at least 9 consecutive days; suitably, during the course of treatment, both compounds will be administered within a specified period for at least 5 consecutive days, followed by administration of Compound $A^2$ alone for at least 5 consecutive days—in this case, the duration of time will be at least 10 consecutive days; suitably, during the course of treatment, both compounds will be administered within a specified period for at least 7 consecutive days, followed by administration of Compound $A^2$ alone for at least 2 consecutive days—in this case, the duration of time will be at least 9 consecutive days; suitably, during the course of treatment, both compounds will be administered within a specified period for at least 14 consecutive days, followed by administration of Compound $A^2$ alone for at least 7 consecutive days—in this case, the duration of time will be at least 21 consecutive days; suitably, during the course of treatment, both compounds will be administered within a specified period for at least 30 consecutive days, followed by administration of Compound $A^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $A^2$ alone for from 3 to 7 consecutive days. Suitably, during the course of treatment, both compounds will be administered within a specified period for from 3 to 6 consecutive days, followed by administration of Compound $A^2$ alone for from 1 to 4 consecutive days. Suitably, during the course of treatment, both compounds will be administered within a specified period for 5 consecutive days, followed by administration of Compound $A^2$ alone for 2 consecutive days. Suitably, during the course of treatment, both compounds will be administered within a specified period for 2 consecutive days, followed by administration of Compound $A^2$ alone for from 3 to 7 consecutive days. Suitably, during the course of treatment, both compounds will be administered within a specified period for from 1 to 3 days over a 7 day period, and during the other days of the 7 day period Compound $A^2$ will be administered alone. Suitably, during the course of treatment, both compounds will be administered within a specified period for 2 days over a 7 day period, and during the other days of the 7 day period Compound $A^2$ will be administered alone. Suitably, during the course of treatment, both compounds will be administered within a specified period for 2 days over a 7 day period, and during the other days of the 7 day period Compound $B^2$ will be administered alone. Suitably, during the course of treatment, both compounds will be administered within a specified period for 1 day over a 7 day period, and during the other days of the 7 day period Compound $B^2$ will be administered alone.

Further regarding "specified period" administration—when Compound $A^2$ and Compound $B^2$ are administered for a specified period, optional additional antineoplastic agents can be administered at any time during the course of treatment or during the duration of time as indicated herein.

Suitably, if the compounds are not administered during a "specified period", they are administered sequentially. By the term "sequential administration", and derivates thereof, as used herein is meant that one of Compound $A^2$ and Compound $B^2$ is administered for one or more consecutive days and the other of Compound $A^2$ and Compound $B^2$ is subsequently administered for one or more consecutive days. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding Sequential Administration:

Suitably, one of Compound $A^2$ and Compound $B^2$ is administered for from 1 to 30 consecutive days, followed by an optional drug holiday, followed by administration of the other of Compound $A^2$ and Compound $B^2$ for from 1 to 30 consecutive days. Suitably, one of Compound $A^2$ and Compound $B^2$ is administered for from 1 to 21 consecutive days, followed by an optional drug holiday, followed by administration of the other of Compound $A^2$ and Compound $B^2$ for from 1 to 21 consecutive days. Suitably, one of Compound $A^2$ and Compound $B^2$ is administered for from 1 to 14 consecutive days, followed by a drug holiday of from 1 to 14 days, followed by administration of the other of Compound $A^2$ and Compound $B^2$ for from 1 to 14 consecutive days. Suitably, one of Compound $A^2$ and Compound $B^2$ is administered for from 2 to 7 consecutive days, followed by a drug holiday of from 2 to 10 days, followed by administration of the other of Compound $A^2$ and Compound $B^2$ for from 2 to 7 consecutive days.

Suitably, Compound $B^2$ will be administered first in the sequence, followed by an optional drug holiday, followed by administration of Compound $A^2$. Suitably, Compound $B^2$ is administered for from 1 to 21 consecutive days, followed by an optional drug holiday, followed by administration of Compound $A^2$ for from 1 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

Suitably, Compound $A^2$ will be administered first in the sequence, followed by an optional drug holiday, followed by administration of Compound $B^2$. Suitably, Compound $A^2$ is administered for from 1 to 21 consecutive days, followed by an optional drug holiday, followed by administration of Compound $B^2$ for from 1 to 21 consecutive days. Suitably, Compound $A^2$ is administered for from 3 to 21 consecutive days, followed by a drug holiday of from 1 to 14 days, followed by administration of Compound $B^2$ for from 3 to 21 consecutive days. Suitably, Compound $A^2$ is administered for from 3 to 21 consecutive days, followed by a drug holiday of from 3 to 14 days, followed by administration of Compound $B^2$ for from 3 to 21 consecutive days. Suitably, Compound $A^2$ is administered for 21 consecutive days, followed by an optional drug holiday, followed by administration of Compound $B^2$ for 14 consecutive days. Suitably, Compound $A^2$ is administered for 14 consecutive days, followed by a drug holiday of from 1 to 14 days, followed by administration of Compound $B^2$ for 14 consecutive days. Suitably, Compound $A^2$ is administered for 7 consecutive days, followed by a drug holiday of from 3 to 10 days, followed by administration of Compound $B^2$ for 7 consecutive days. Suitably, Compound $A^2$ is administered for 3 consecutive days, followed by a drug holiday of from 3 to 14 days, followed by administration of Compound $B^2$ for 7 consecutive days. Suitably, Compound $A^2$ is administered for 3 consecutive days, followed by a drug holiday of from 3 to 10 days, followed by administration of Compound $B^2$ for 3 consecutive days. Suitably, Compound $A^2$ is administered for 7 consecutive days, followed by administration of Compound $B^2$ for 1 day. Suitably, Compound $A^2$ is administered for 6 consecutive days, followed by administration of Compound $B^2$ for 1 day. Suitably, Compound $B^2$ is administered for 1 day, followed by administration of Compound $A^2$ for 7 consecutive days. Suitably, Compound $B^2$ is administered for 1 day, followed by administration of Compound $A^2$ for 6 consecutive days.

Further regarding "sequential administration"—when Compound $A^2$ and Compound $B^2$ are administered sequentially, optional additional antineoplastic agents can be administered at any time during the course of treatment.

It is understood that a "specified period" administration and a "sequential" administration can be followed by repeat dosing or can be followed by an alternate dosing protocol, and a drug holiday may precede the repeat dosing or alternate dosing protocol.

Suitably, the amount of Compound $A^2$ administered as part of the combination according to the present invention will be an efficacious, non toxic amount administered from 1 to 4 times a day. Suitably, the selected amount of Compound $A^2$ is administered twice a day. Suitably, the selected amount of Compound $A^2$ is administered once a day. Suitably, the selected amount of Compound $A^2$ is administered once a week intravenously. Suitably, the selected amount of Compound $A^2$ is administered twice a week intravenously.

Suitably, Compound $A^2$ is Velcade® and is administered intravenously once or twice a week. Suitably, Compound $A^2$ is Velcade® and is administered intravenously once or twice a week in an amount selected from 0.5 to 1.3 mg/m$^2$. Suitably, Compound $A^2$ is Velcade® and is administered intravenously once or twice a week in an amount of 1 mg/m$^2$. Suitably, Compound $A^2$ is Velcade® and is administered intravenously once or twice a week in an amount of 1.3 mg/m$^2$. Suitably, Compound $A^2$ is Velcade® and is administered intravenously once or twice a week in an amount of 0.6 mg/m$^2$. Suitably, Compound $A^2$ is Velcade® and is administered intravenously once or twice a week in an amount of 0.7 mg/m$^2$. Suitably, Compound $A^2$ is Velcade® and is administered intravenously once or twice a week in an amount of 0.8 mg/m$^2$. Suitably, Compound $A^2$ is Velcade® and is administered intravenously once or twice a week in an amount of 0.9 mg/m$^2$.

Suitably, Compound $A^2$ is Velcade® and is administered subcutaneously once or twice a week. Suitably, Compound $A^2$ is Velcade® and is administered subcutaneously once or twice a week in an amount selected from 0.5 to 1.3 mg/m$^2$. Suitably, Compound $A^2$ is Velcade® and is administered subcutaneously once or twice a week in an amount of 1 mg/m$^2$. Suitably, Compound $A^2$ is Velcade® and is administered subcutaneously once or twice a week in an amount of 1.3 mg/m$^2$. Suitably, Compound $A^2$ is Velcade® and is administered subcutaneously once or twice a week in an amount of 0.6 mg/m$^2$. Suitably, Compound $A^2$ is Velcade® and is administered subcutaneously once or twice a week in an amount of 0.7 mg/m$^2$. Suitably, Compound $A^2$ is Velcade® and is administered subcutaneously once or twice a week in an amount of 0.8 mg/m$^2$. Suitably, Compound $A^2$ is Velcade® and is administered subcutaneously once or twice a week in an amount of 0.9 mg/m$^2$.

Suitably, Compound $A^2$ is Velcade® and is administered as part of the combination intravenously or subcutaneously once or twice a week in an amount selected from about 1.35 to 2.0 mg/m$^2$, suitably the selected amount of Velcade® is administered once a week. Suitably, Compound $A^2$ is Velcade® and is administered as part of the combination intravenously or subcutaneously once or twice a week in an amount of 1.35 mg/m$^2$, suitably the selected amount of Velcade® is administered once a week. Suitably, Compound $A^2$ is Velcade® and is administered as part of the combination intravenously or subcutaneously once or twice a week in an amount of 1.4 mg/m$^2$, suitably the selected amount of Velcade® is administered once a week. Suitably, Compound $A^2$ is Velcade® and is administered as part of the combination intravenously or subcutaneously once or twice a week in an amount of 1.45 mg/m$^2$, suitably the selected amount of Velcade® is administered once a week. Suitably, Compound $A^2$ is Velcade® and is administered as part of the combination intravenously or subcutaneously once or twice a week in an amount of 1.5 mg/m$^2$, suitably the selected amount of Velcade® is administered once a week. Suitably, Compound $A^2$ is Velcade® and is administered as part of the combination intravenously or subcutaneously once or twice a week in an amount of 1.55 mg/m$^2$, suitably the selected amount of Velcade® is administered once a week. Suitably, Compound $A^2$ is Velcade® and is administered as part of the combination intravenously or subcutaneously once or twice a week in an amount of 1.6 mg/m$^2$, suitably the selected amount of Velcade® is administered once a week. Suitably, Compound $A^2$ is Velcade® and is administered as part of the combination intravenously or subcutaneously once or twice a week in an amount of 1.65 mg/m$^2$, suitably the selected amount of Velcade® is administered once a week. Suitably, Compound $A^2$ is Velcade® and is administered as part of the combination intravenously or subcutaneously once or twice a week in an amount of 1.7 mg/m$^2$, suitably the selected amount of Velcade® is administered once a week. Suitably, Compound $A^2$ is Velcade® and is administered as part of the combination intravenously or subcutaneously once or twice a week in an amount of 1.75 mg/m$^2$, suitably the selected amount of Velcade® is administered once a week. Suitably, Compound $A^2$ is Velcade® and is administered as part of the combination intravenously or subcutaneously once or twice a week in an amount of 1.8 mg/m$^2$, suitably the selected amount of Velcade® is administered once a week. Suitably, Compound $A^2$ is Velcade® and is administered as part of the combination intravenously or subcutaneously once or twice a week in an amount of 1.85 mg/m$^2$, suitably the selected amount of Velcade® is administered once a week. Suitably, Compound $A^2$ is Velcade® and is administered as part of the combination intravenously or subcutaneously once or twice a week in an amount of 1.9 mg/m$^2$, suitably the selected amount of Velcade® is administered once a week. Suitably, Compound $A^2$ is Velcade® and is administered as part of the combination intravenously or subcutaneously once or twice a week in an amount of 1.95 mg/m$^2$, suitably the selected amount of Velcade® is administered once a week. Suitably, Compound $A^2$ is Velcade® and is administered as part of the combination intravenously or subcutaneously once or twice a week in an amount of 2.0 mg/m$^2$, suitably the selected amount of Velcade® is administered once a week.

Suitably, the amount of Compound $B^2$ administered as part of the combination according to the present invention will be an amount selected from about 5 mg to about 500 mg; suitably, the amount will be selected from about 25 mg to about 400 mg; suitably, the amount will be selected from about 30 mg to about 375 mg; suitably, the amount will be selected from about 35 mg to about 350 mg; suitably, the amount will be selected from about 40 mg to about 300 mg; suitably, the amount will be selected from about 45 mg to about 275 mg; suitably, the amount will be selected from about 50 mg to about 250 mg; suitably, the amount will be selected from about 55 mg to about 225 mg; suitably, the amount will be selected from about 60 mg to about 200 mg; suitably, the amount will be selected from about 65 mg to about 175 mg; suitably, the amount will be selected from about 70 mg to about 150 mg; suitably, the amount will be selected from about 50 mg to about 300 mg; suitably, the amount will be selected from about 75 mg to about 150 mg; suitably, the amount will be about 100 mg. Accordingly, the amount of Compound $B^2$ administered as part of the combination according to the present invention will be an amount selected from about 5 mg to about 500 mg. For example, the amount of Compound $B^2$ administered as part of the combination according to the present invention can be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 175 mg, 200 mg, 225 mg, 250 mg, 275 mg, 300 mg, 325 mg, 350 mg, 375 mg, 400 mg, 425 mg, 450 mg, 475 mg or 500 mg. Suitably, the selected amount of Compound $B^2$ is administered twice a day. Suitably, the selected amount of Compound $B^2$ is administered once a day.

As used herein, all amounts specified for Compound $A^2$ and Compound $B^2$ are indicated as the administered amount of free or unsalted compound per dose.

The method of the present invention may also be employed with other therapeutic methods of cancer treatment.

While it is possible that, for use in therapy, therapeutically effective amounts of the combinations of the present invention may be administered as the raw chemical, it is preferable to present the combinations as a pharmaceutical composition or compositions. Accordingly, the invention further provides pharmaceutical compositions, which include Compound $A^2$ and/or Compound $B^2$, and one or more pharmaceutically acceptable carriers. The combinations of the present invention are as described above. The carrier(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical formulation including admixing Compound $A^2$ and/or Compound $B^2$ with one or more pharmaceutically acceptable carriers. As indicated above, such elements of the pharmaceutical combination utilized may be presented in separate pharmaceutical compositions or formulated together in one pharmaceutical formulation.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

Compound $A^2$ and Compound $B^2$ may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that Compound $A^2$ and Compound $B^2$ may be compounded together in a pharmaceutical composition/formulation. Suitably, Compound $A^2$ and Compound $B^2$ are administered in separate pharmaceutical compositions.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

As indicated, therapeutically effective amounts of the combinations of the invention (Compound $A^2$ in combination with Compound $B^2$) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attending physician.

Figure 1:
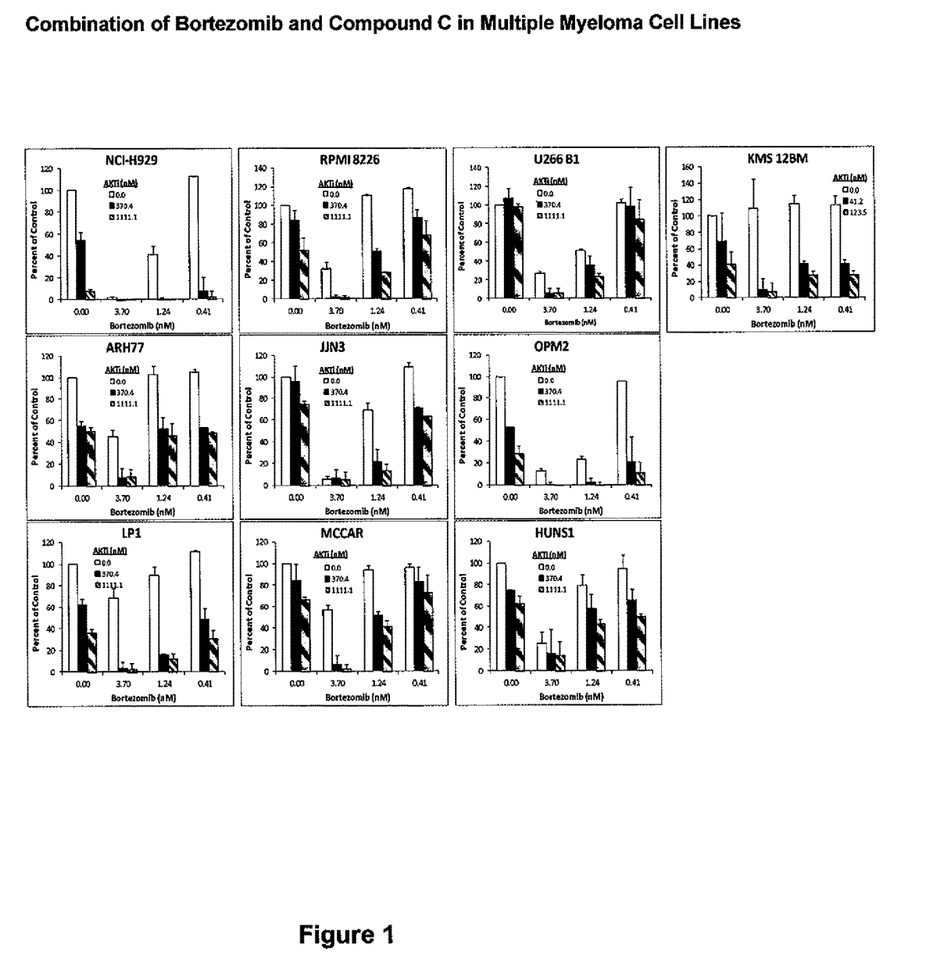
FIG. 1 shows the combination of bortezomib and Compound C in Multiple Myeloma Cell Lines.
Figure 2:
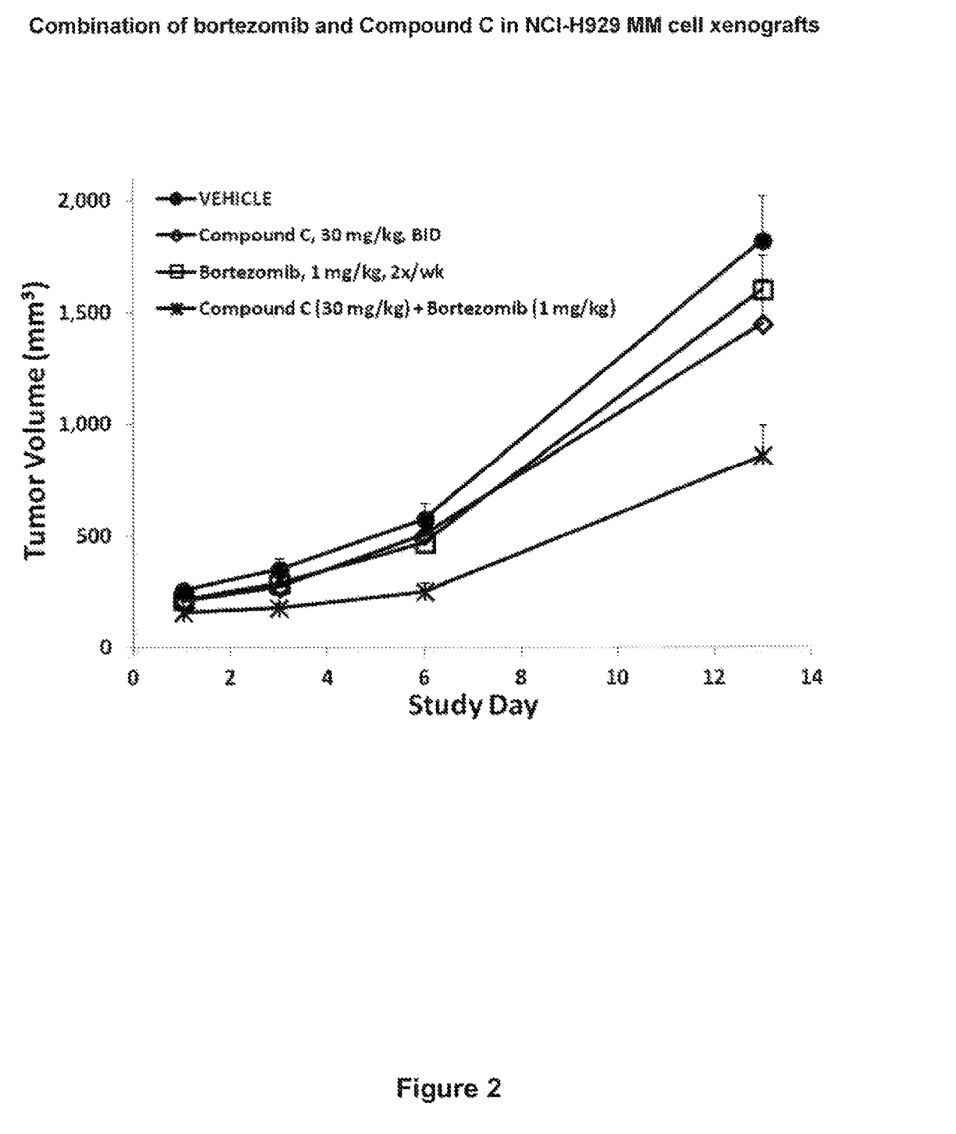
FIG. 2 shows the combination of bortezomib and Compound C in NCI-H929 Multiple Myeloma cell xenografts.
Figure 3:
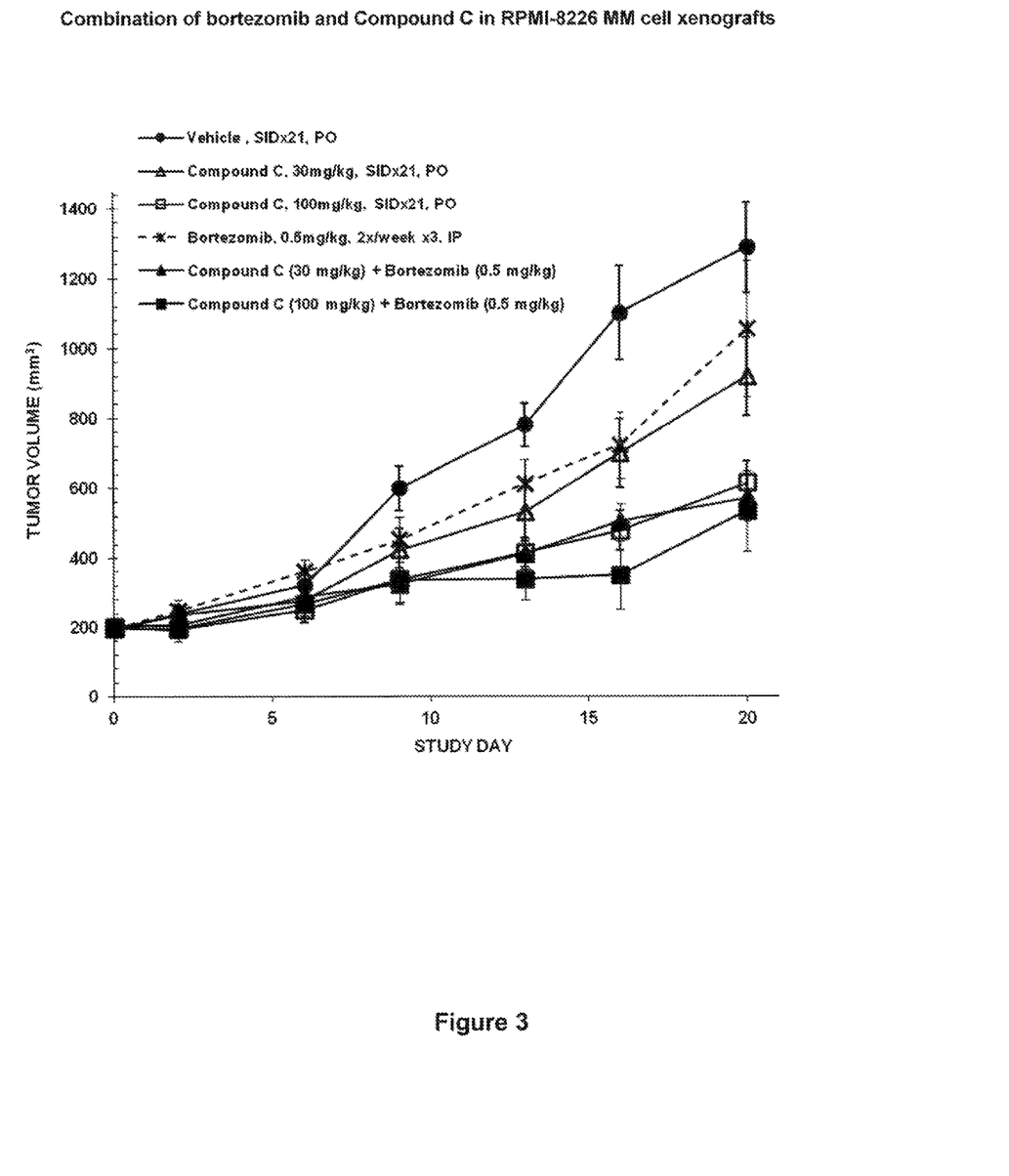
FIG. 3 shows the Combination of bortezomib and Compound C in RPMI-8226 Multiple Myeloma cell xenografts.

The combinations of the invention are tested for efficacy, advantageous and synergistic properties generally according to known procedures. For example:

Method:

Female SCID mice are implanted subcutaneously with $1\times10^6$ NCI-H929 cells or small tumor fragments arising from RPMI-8226 cells (both human multiple myeloma). When the tumor volume reaches 200-300 mm$^3$, mice are block randomized to different treatment groups (n=8 mice/group). Mice receive AKT inhibitor, Compound B (in this assay, Compound B, is used in the form of the hydrochloride salt), at 30 or 100 mg/kg, once daily (SID) for the duration of study or 30 mg/kg, twice daily (BID) for the duration of study in 20% PEG-400, 1% DMSO in water by oral gavage. Compound $A^2$ is administered at 0.5 or 1.0 mg/kg, intraperitoneally at twice/week for the duration of study either alone or in combination with Compound B. Optional additional antineoplastic agents may also be added. Mice are weighed and tumors measured by calipers twice weekly. Tumor volumes are calculated using the formula: tumor volume=(Length×Width$^2$)/2. The percentage of tumor growth inhibition is calculated on each day of tumor measurement using the formula: 100×[1−(average growth of the compound-treated tumors/average growth of vehicle-treated control tumors)]. Data is plotted as mean±sem for tumor volume for each group and is reported in FIGS. 1 to 3 below.

Generally, the combinations of the present invention are tested for efficacy, advantageous and synergistic properties according to known procedures such as described below.

Suitably, the combinations of the invention are tested for efficacy, advantageous and synergistic properties generally according to the following combination cell proliferation assays. Cells are plated in 96 or 384-well plates at 500-5000 cells/well in culture media appropriate for each cell type, supplemented with 10% FBS and 1% penicillin/streptomycin, and incubated overnight at 37° C., 5% $CO_2$. Cells are treated in a grid manner with dilution of Compound $A^2$ (8 dilutions, including no compound, of 3-fold dilutions starting from 0.1-30 µM depending on combination) from left to right on 96-well plate and also treated with Compound $B^2$ (8 dilutions, including no compound, of 3-fold dilutions starting from 1-30 µM depending on combination) from top to bottom on 96-well plate and incubated as above for a further 72 hours. Optional additional antineoplastic agents may also be added. In some instances compounds are added in a staggered manner and incubation time can be extended up to 7 days. Cell growth is measured using CellTiter-Glo® reagent according to the manufacturer's protocol and signals are read on a PerkinElmer EnVision™ reader set for luminescence mode with a 0.5-second read. Data are analyzed as described below.

Results are expressed as a percentage of control (untreated cells) and decrease in signal for each single agent at various concentrations is compared with the combination treatment at respective single agent concentrations. Alternatively, the results are expressed as a percentage of the t=0 value and plotted against compound(s) concentration. The t=0 value is normalized to 100% and represents the number of cells present at the time of compound addition. The cellular response is determined for each compound and/or compound combination using a 4- or 6-parameter curve fit of cell viability against concentration using the IDBS XLfit plug-in for Microsoft Excel software and determining the concentration required for 50% inhibition of cell growth ($gIC_{50}$). Background correction is made by subtraction of values from wells containing no cells. For each drug combination a Combination Index (CI), Excess Over Highest Single Agent (EOHSA) and Excess Over Bliss (EOBliss) are calculated according to known methods such as described in Chou and Talalay (1984) Advances in Enzyme Regulation, 22, 37 to 55; and Berenbaum, MC (1981) Adv. Cancer Research, 35, 269-335.

Because the combinations of the present invention are active in the above assays they exhibit advantageous therapeutic utility in treating cancer.

Suitably, the present invention relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the present invention relates to a method for treating or lessening the severity of a cancer selected from: brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Suitably, the present invention relates to a method for treating or lessening the severity of multiple myeloma.

This invention provides a combination comprising a proteasome inhibiting compound, suitably bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, and optional additional antineoplastic agents.

This invention also provides for a combination comprising bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof.

This invention also provides for a combination comprising bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, for use in treating cancer.

This invention also provides a pharmaceutical composition comprising a combination of bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof.

This invention also provides a combination kit comprising a proteasome inhibiting compound, suitably bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, and optional additional antineoplastic agents.

This invention also provides for the use of a combination comprising a proteasome inhibiting compound, suitably bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, in the manufacture of a medicament.

This invention also provides for the use of a combination comprising a proteasome inhibiting compound, suitably bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, in the manufacture of a medicament to treat cancer.

This invention also provides a method of treating cancer which comprises administering a combination of a proteasome inhibiting compound, suitably bortezomib, and N-{(1S)-2-amino-1-[(3-fluorophenyl)methyl]ethyl}-5-chloro-4-(4-chloro-1-methyl-1H-pyrazol-5-yl)-2-thiophenecarboxamide, or a pharmaceutically acceptable salt, suitably the hydrochloride salt, thereof, and optional additional antineoplastic agents to a subject in need thereof.

The following examples are intended for illustration only and are not intended to limit the scope of the invention in any way.

Experimental Details

Example 1—Capsule Composition

An oral dosage form for administering a combination of the present invention is produced by filling a standard two piece hard gelatin capsule with the ingredients in the proportions shown in Table I, below.

TABLE I

| INGREDIENTS | AMOUNTS |
| --- | --- |
| (Compound $A^2$) | 3.5 mg |
| N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) | 72 mg |
| Mannitol | 250 mg |
| Talc | 125 mg |
| Magnesium Stearate | 8 mg |

Example 2—Capsule Composition

An oral dosage form for administering one of the compounds of the present invention is produced by filing a standard two piece hard gelatin capsule with the ingredients in the proportions shown in Table II, below.

TABLE II

| INGREDIENTS | AMOUNTS |
| --- | --- |
| (Compound $A^2$) | 4 mg |
| Mannitol | 150 mg |
| Talc | 16 mg |
| Magnesium Stearate | 4 mg |

Example 3—Capsule Composition

An oral dosage form for administering one of the compounds of the present invention is produced by filing a standard two piece hard gelatin capsule with the ingredients in the proportions shown in Table III, below.

TABLE III

| INGREDIENTS | AMOUNTS |
| --- | --- |
| N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) | 72 mg |
| Mannitol | 150 mg |
| Talc | 12 mg |
| Magnesium Stearate | 8 mg |

Example 4—Tablet Composition

The sucrose, microcrystalline cellulose and the compounds of the invented combination, as shown in Table IV below, are mixed and granulated in the proportions shown with a 10% gelatin solution. The wet granules are screened, dried, mixed with the starch, talc and stearic acid, then screened and compressed into a tablet.

TABLE IV

| INGREDIENTS | AMOUNTS |
| --- | --- |
| (Compound $A^2$) | 3 mg |
| N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) | 72 mg |
| Microcrystalline cellulose | 300 mg |
| sucrose | 10 mg |
| starch | 40 mg |
| talc | 20 mg |
| stearic acid | 5 mg |

Example 5—Tablet Composition

The sucrose, microcrystalline cellulose and one of the compounds of the invented combination, as shown in Table V below, are mixed and granulated in the proportions shown with a 10% gelatin solution. The wet granules are screened, dried, mixed with the starch, talc and stearic acid, then screened and compressed into a tablet.

TABLE V

| INGREDIENTS | AMOUNTS |
| --- | --- |
| (Compound $A^2$) | 4 mg |
| Microcrystalline cellulose | 200 mg |
| sucrose | 4 mg |
| starch | 2 mg |
| talc | 1 mg |
| stearic acid | 0.5 mg |

Example 6—Tablet Composition

The sucrose, microcrystalline cellulose and one of the compounds of the invented combination, as shown in Table VI below, are mixed and granulated in the proportions shown with a 10% gelatin solution. The wet granules are screened, dried, mixed with the starch, talc and stearic acid, then screened and compressed into a tablet.

TABLE VI

| INGREDIENTS | AMOUNTS |
| --- | --- |
| N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) | 72 mg |
| Microcrystalline cellulose | 300 mg |
| sucrose | 40 mg |
| starch | 20 mg |
| talc | 10 mg |
| stearic acid | 5 mg |

Example 7—Injectable Parenteral Composition

An injectable form for administering a presently invented combinations is produced by stirring 1.5% by weight of (Compound $A^2$) and N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) in 10% by volume propylene glycol in water.

Example 8—Injectable Parenteral Composition

An injectable form for administering a compound of the presently invented combinations is produced by stirring 1.5% by weight of (Compound $A^2$) in 10% by volume propylene glycol in water.

Example 9—Injectable Parenteral Composition

An injectable form for administering a compound of the presently invented combinations is produced by stirring

1.5% by weight of N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (the hydrochloride salt of Compound B) in 10% by volume propylene glycol in water.

While the preferred embodiments of the invention are illustrated by the above, it is to be understood that the invention is not limited to the precise instructions herein disclosed and that the right to all modifications coming within the scope of the following claims is reserved.

I claim:

1. A method of treating cancer in a subject in need thereof which comprises the in vivo administration of a combination comprising:

(i) a compound of Structure (I):

and (ii) a compound of Structure (II):

in the form of a monohydrochloride salt, to such subject, wherein the amount of the compound of Structure (I) is selected from 0.5 to 1.0 mg/kg and that amount is administered intravenously or subcutaneously twice per week, wherein the amount of the compound of Structure (II) is 30 mg/kg, administered once per day or twice per day, wherein the combination is administered for a duration of time of between 1 and 30 days, and wherein the cancer is multiple myeloma.

2. A method according to claim 1, wherein the combination comprises one or more pharmaceutically acceptable carriers.

* * * * *

UNITED STATES PATENT AND TRADEMARK OFFICE
CERTIFICATE OF CORRECTION

PATENT NO. : 10,449,226 B2  
APPLICATION NO. : 15/385205  
DATED : October 22, 2019  
INVENTOR(S) : Rakesh Kumar Page 1 of 1

It is certified that error appears in the above-identified patent and that said Letters Patent is hereby corrected as shown below:

On the Title Page

Column 1, Line 4, item [63], under "Related U.S. Application Data", delete "and" and insert -- which is --.

Column 2, Line 15, item [56], under "OTHER PUBLICATIONS", delete "Chern." and insert -- Chem. --.

Signed and Sealed this  
Seventeenth Day of December, 2019

Andrei Iancu  
*Director of the United States Patent and Trademark Office*